United States Patent [19]
Pershadsingh et al.

[11] Patent Number: 5,866,595
[45] Date of Patent: Feb. 2, 1999

[54] CALCIUM ANTAGONISTS FOR TREATMENT OF VASCULAR RESTENOSIS

[75] Inventors: Harrihar A. Pershadsingh, Bakersfield; Theodore W. Kurtz, Mill Valley, both of Calif.

[73] Assignee: The Regents of The University of California, Oakland, Calif.

[21] Appl. No.: 337,340

[22] Filed: Nov. 10, 1994

Related U.S. Application Data

[63] Continuation of Ser. No. 206,909, Mar. 4, 1994, abandoned, which is a continuation of Ser. No. 766,727, Sep. 26, 1991, abandoned.

[51] Int. Cl.$^6$ .................................................. A61K 31/425
[52] U.S. Cl. ......................... 514/369; 514/299; 514/340; 514/342; 514/365; 514/366; 514/367; 514/370
[58] Field of Search ..................... 514/369, 370, 514/342, 340, 367, 366, 365, 299

[56] References Cited

U.S. PATENT DOCUMENTS

| | | | |
|---|---|---|---|
| 4,175,130 | 11/1979 | Yamanaka et al. | 424/270 |
| 4,346,088 | 8/1982 | Lang et al. | 514/211 |
| 4,728,739 | 3/1988 | Kees et al. | 548/183 |
| 4,791,125 | 12/1988 | Clark | 514/369 |
| 4,798,835 | 1/1989 | Krupp et al. | 514/369 |
| 5,053,420 | 10/1991 | Pershadsingh | 514/369 |
| 5,095,027 | 3/1992 | Goldberg et al. | 514/425 |
| 5,252,735 | 10/1993 | Morris | 544/121 |

OTHER PUBLICATIONS

Chemical Abstracts An 108: 129343. Haragun et al. "Pradipocyte differentiation in vitro: identification of a highly active adipogenic agent," J. Cell. Physiol. , (1988), 134 (1), 124–30.

Meuck Manual pp. 386–387, 1038–1039, 1982.

Pershadsingh & McDonald, "Hormone–receptor coupling and the molecular mechanism of insulin action in the adippococyte: a Paradigim for Ca $^2$homeostasis in the initiation of the insulin–induced metabolic cascade"Cell Calcium 5: 111–130, 1994

Colca et al. "Ciglitazone . . . " Metabolism vol 37 (3): 276–280 (1980).

*Primary Examiner*—Keith D. MacMillan
*Attorney, Agent, or Firm*—Townsend and Townsend and Crew, LLP

[57] ABSTRACT

According to the present invention, compounds selected from the thiozole class of organic molecules are employed as antagonists for receptor-operated ion channels (ROICs) useful in the treatment of a variety of disease states in which ROICs are implicated. ROICs of particular interest are receptor-operated calcium channels (ROCCs). Compounds of particular interest with respect to the subject invention are compounds of the thiazolidinedione class of organic molecules, more particularly ciglitazone. Disease states in which particular utility is expected include vasculoproliferative diseases such as atherosclerosis, restenosis following angioplasty, and other conditions in which PDGF is known to play a role. The utility of the present invention with respect to further studies on the operation of ROICs and ROCCs and their role in disease will be apparent to those of skill in the art.

11 Claims, 1 Drawing Sheet

CALCIUM ANTAGONISTS FOR TREATMENT OF VASCULAR RESTENOSIS

This is a Continuation of application Ser. No. 08/206,909, filed Mar. 4, 1994 (now abandoned), which is a continuation of application Ser. No. 07/766,727, filed Sep. 26, 1991 (abandoned).

BACKGROUND OF THE INVENTION

1. Field of the Invention

The present invention relates generally to the treatment of disease and, more particularly, to the treatment of diseases associated with receptor-operated calcium channels, including the treatment of hypertension, atherosclerosis, atherogenesis, thrombosis, vasospasm, and the consequences of these conditions.

Agonist-mediated increases in intracellular calcium in mammalian cells can occur via multiple mechanisms, most notably increased conductance of $Ca^{2+}$ ions through voltage-operated calcium channels (VOCCs) and receptor-operated calcium channels (ROCCs), both being located in the plasma membrane.

The VOCCs were the first identified in cardiac muscle and their characterization were greatly facilitated by the discovery of the highly sensitive and specific dihydropyridine antagonists. Fleckenstein et al., *Am. J. Cardiol.* (1987) 59:177B–187B. These channels occur primarily in so-called electrically excitable cells and have been studied extensively in cardiac, smooth, and skeletal muscle. Channel opening, or more precisely, the probability that specified numbers of calcium channels are biophysically in the open state, is directly related to the potential difference across the plasma membrane. Depolarization increases the probability of the existence of VOCCs in the open state, whereas hyperpolarization results in the opposite, that VOCCs are likely to be closed.

The ROCCs, on the other hand are insensitive to changes in membrane potential and although sensitivity to dihydropyridine antagonists have been reported, the concentration required for significant blockade are orders of magnitude greater than those required for antagonism of VOCCs. ROCCs are activated by specific ligands and have been identified in all mammalian cell types examined including electrically excitable cells, e.g. cardiac and vascular smooth muscle. ROCCs have been identified in cells not ordinarily thought of being electrically excitable (Table 1).

The activity of ROCCs appear to be modulated primarily through agonist interaction with specific cell surface receptors with consequent phosphinositide breakdown and induction by inositol phosphates, e.g. inositol trisphosphate and inositol tetrakisphosphate, and activation of calcium entry via ROCCs. Ligands that transmit their biological signals by mechanisms involving calcium entry via ROCCs produce a transient increase in intracellular calcium concentration ($[Ca^{2+}]i$) typified by a characteristic time-dependent kinetic form, regardless of the particular chemical agonist or the cell (tissue) type.

TABLE I

Disease processes and potential sites of lesions where receptor-operated calcium channel antagonists are expected to function to offset the particular lesion(s)

| Pathophysiologic processes, Disease states | Tissues | Neurohumoral agents |
|---|---|---|
| Atherogenesis, Atherosclerosis, | VSM, endothelium | growth factors, A II endothelin, cytokines, |
| Vasospasm, Angina Pectoris | | PDGF, thrombin |
| Restenosis after angioplasty | VSM, endothelium | PDGF, growth factors |
| Thrombosis & infarction | VSM, platelets | PDGF, thrombin, A II, endothelium, EGF, TGF-beta |
| Hypertension | VSM cell, endothelium, autonomic innervation, juxtaglomerular | vasopressors, EDRF, neurotransmitters, endothelins |
| Neoplasia and oncogenesis | various | transforming growth, factors, endothelin, PDGF |
| Immunodeficient conditions | T cell, B cell, mast cells, eosinophil neutrophil, macrohage | immune response modifiers, cytokines chemotactic peptides |
| Wound-healing | mesenchyme and other cells | growth factors, cell adhesion molecules |
| Reactive airway disease, asthma allergy | bronchial VSM cell & endothelium, mast cells, | histamine, endothelin, beta-2 agonists, cromolyn |
| Neural dysfunction glioblastoma | glial cells, others | neurotransmitters nerve growth and other factors, endothelin |
| Schizophrenia | CNS | endothelin |
| Encephalopathy | CNS | neuropeptides, amino acids, nitric oxide |
| Memory dysfuncton Organogenesis | CNS, other neural cells various | neurotransmitters colony-stimulating and chemotactic factors, neuropeptides |
| Endometriosis | endometrial cells | PDGF, other growth factors |
| Algesia | CNS | kinin/kininogen modulators |

VSM = vascular smooth muscle; EDRF = endothelium-derived relaxing factor; TGF-beta = transforming growth factor; A II = angiotensin II; EGF = epidermal growth factor Subsequent to agonist-receptor binding, depending on the activator, there is a sharp initial spike in $[Ca^{2+}]i$ either immediately or after a delay followed by a slow decay in the calcium signal, which may be followed in some cases by oscillatory excursions in the calcium signal. Depending on cell-type or agonist, this general form has subtle but important variations, and may represent different subtypes of receptor-operated channels (see "Experimental Findings" below, and Ref: Rink, FEBS Lett, 1990).

A first aspect of the invention focuses on two physiological ligands that function via modulation of ROCCs and are implicated in the pathogenesis of hypertension, atherogenesis and atherosclerosis and other vasculoproliferative disease.

A second aspect of the invention includes the general implications of the role of ROCCs in the pathophysiological derangements in a variety of cellular functions, including those involving, neoplasia, immune response modification, endocrine and exocrine dysfunction, neuropsychiatric disease, wound-healing, and cell growth and proliferation in diverse organ systems. These vast implications will be disclosed in the context of small neurohumoral peptides, particularly platelet-derived growth factor (PDGF) and bradykinin.

A further aspect of the invention includes the utility of the subject use of thiazole compounds as antagonists for ROCCs in the further illucidation of ROCC operation.

A still further aspect of the invention includes the use of thiazole compounds in the treatment of disease in humans such as atherosclerosis.

SUMMARY OF THE INVENTION

According to the present invention, compounds selected from the thiazole class of organic molecules are employed as antagonists for receptor-operated ion channels (ROICs) useful in the treatment of a variety of disease states in which ROICs are implicated. ROICs of particular interest are receptor-operated calcium channels (ROCCs). Compounds of particular interest with respect to the subject invention are compounds of the thiazolidinedione class of organic molecules, more particularly ciglitazone. Disease states in which particular utility is expected include vasculoproliferative diseases such as atherosclerosis, restenosis following angioplasty, and other conditions in which PDGF is known to play a role. The utility of the present invention with respect to further studies on the operation of ROICs and ROCCs and their role in disease will be apparent to those of skill in the art.

DETAILED DESCRIPTION OF THE INVENTION

Figure 1:
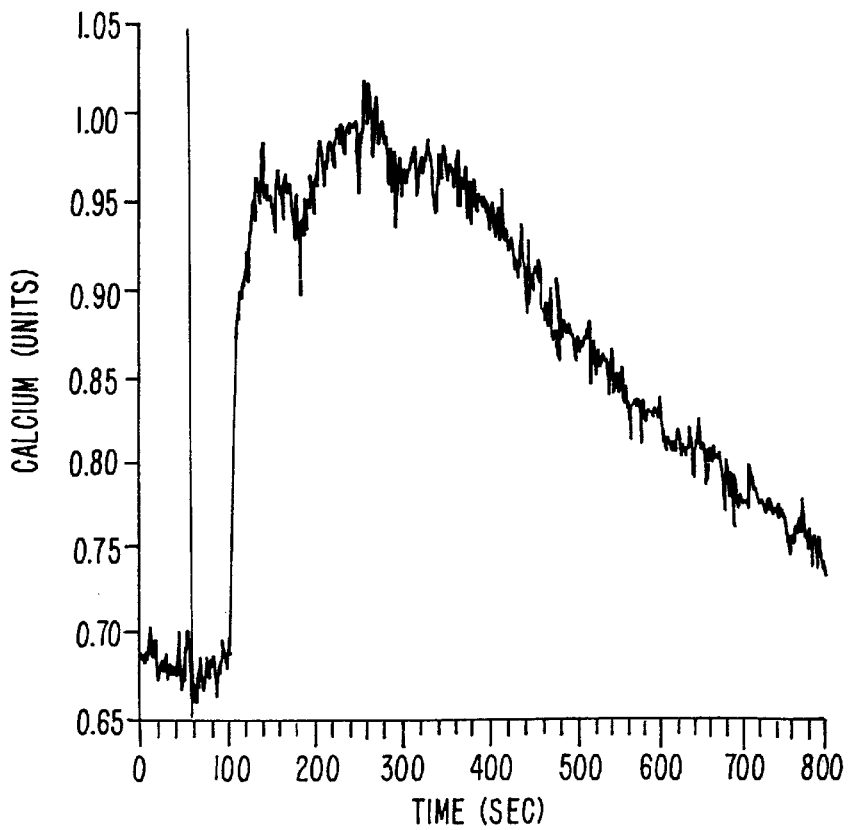
FIG. 1 shows the effect of PDGF on $[Ca^{2+}]i$ on A172 cells.

The compounds employed according to the subject invention, the thiazole class of organic compounds, are the subject of extensive disclosure in the literature and methods of synthesis are, therefore, known to those of skill in the art. Of particular interest, however, are the disclosures of U.S. application Ser. No. 07/421,102, filed 13 Oct. 1989 and U.S. application Ser. No. 07/725,327, filed 8 Jul. 1991, the disclosures of which are hereby incorporated by reference.

The compounds of the subject invention are useful as antagonists of ROCCs which are implicated in a variety of tissues as indicated in Table II. The role of ROCCs in disease is only now being illucidated. For example, it is believed that the neurodegenerative effects of the human immunodeficiency virus (HIV) seen in many HIV infecteed patients is the result of the dysfunction of ROCCs in neurol tissue wherein the virus holds open ROCCs, causing the target cell to "flood" with calcium and ultimately die. The utility of ROCCs antagonists is obvious in such a condition.

According to the subject invention, ROCC antagonists are useful in modifying the effect of certain growth factors, particularly PDGF. PDGF is implicated in a variety of cardiovascular disease states including atherosclerosis, unstable angina, and restenosis following angioplasty. Monoclonal antibodies to PDGF have been shown to inhibit neointimal smooth muscle accumulation following angioplasty. Gordon, et al., *Science*(1991)253:1129–32. It is believed that efficacous doses of the compounds of the subject invention would have a similar effect on disease states wherein PDGF is implicated. An efficacous dose would be in the range of about 0.2 mg/kg to 100 mg/kg, particularly about 1 mg/kg to about 50 mg/kg, and more particularly about 2 mg/kg to 20 mg/kg. Efficacy is defined as the modification of calcium or other ion transport across the cell membrane of host cells from the level of ion transport prior to the administration of the therapeutic agent.

TABLE II

Tissue Diversity of Ligand-Activated, Receptor-Operated Calcium Channels in Mammalian Cells (Partial List)

| Cell/Tissue | Agonist (examples) |
|---|---|
| Human T lymphocyte | PHA, antibodies to CD2, CD3 and T cell receptor epitopes |
| Human B lymphocyte | anti Ig antibodies, PHA |
| Human mast cell | histamine |
| Human platelet | thrombin, ADP |
| Vascular smooth muscle | norepinephrine, PDGF, endothelin-1, histamine, vasopressin, angiotensin |
| Ileum smooth muscle | acetylcholine |
| Human A172 glioma cell | bradykinin, PDGF |
| Vascular endothelium | thrombin, histamine EDRF, nitric oxide |
| Hepatocyte | vasopressin |
| Lacrimal acinar cell | acetylcholine |
| Neutrophil | fMLP |
| J774 macrophage | ATP |
| Neural cells | neurotransmitters endothelin-1, endothelin-3 |
| Bronchial smooth muscle | endothelin-1 |
| Glomerular mesangial cells | endothelin |
| Parotid cell | muscarinic agonists |
| Human glioma | endothelin |

PHA = phytohemaglutinin; Ig = immunoglobulin; fMLP = formyl-methionyl-leucyl-phenylalanine; ATP = adenosine triphosphate; EDRF = endothelium-derived relaxing factor; ADP = adenosine diphosphate

EXPERIMENTAL

MATERIALS AND METHODS

A. Effect of ciglitazone on the receptor-operated calcium channel agonist-induced $[Ca^{2+}]i$ signal.

The A172 human glioblastoma cell line was chosen to test the above-stated hypothesis for three reasons. First, the effects of PDGF on $[Ca^{2+}]i$ in A172 cells has been studied in detail. Second, the A172 cell does not contain voltage-sensitive calcium channels. Third, PDGF was chosen for its diverse cellular effects, including vasoconstriction, chemotaxis, and cell growth. Unless indicated otherwise, the methods employed in these studies are identical to those described in Szollosi et al., *Cell Calcium* (1991)12:477–91, the disclosures of which are hereby incorporated by reference.

A172 cells were grown to approximately 95% confluence and serum-starved for 4.5 hr prior to loading with the intracellular calcium indicator indo 1 by exposure to 3 μM of the acetoxymethyl ester (indo 1-AM). Ciglitazone, dissolved in dimethylsulfoxide, was added to a final concentration of 2 μg/ml immediately before loading with indo 1. The cells were incubated at 37 degrees for 45 min in an humidified incubator with 95% air plus 5% $CO_2$ as gas phase. The extracellular fluid was removed, the cells washed thrice with serum-free medium, and reincubated for a further 30 min to ensure complete hydrolysis of the indo 1-AM. The cells were then analyzed individually in a laser scanning microspectrophotofluorometer.

The effects of PDGF on $[Ca^{2+}]i$ on A172 cells are shown in FIG. 1. The data shown is the sum of the signal obtained by scanning 8 adjacent cells. The vertical bar signifies the time at which PDGF (20 ng/ml) was added to the well containing the cells. There is an initial delay followed by a sharp rise in $[Ca^{2+}]i$. The peak value was sustained for approximately 3 min and is followed by a slow, sustained decay in the calcium signal. The proof that the initial spike in Al 72 cells is caused by the release of calcium from intracellular stores, and that the secondary sustained phase is the result of calcium entry via calcium channels located in the plasma membrane, is described in detail by Szollosi, et al.

Figure 2:
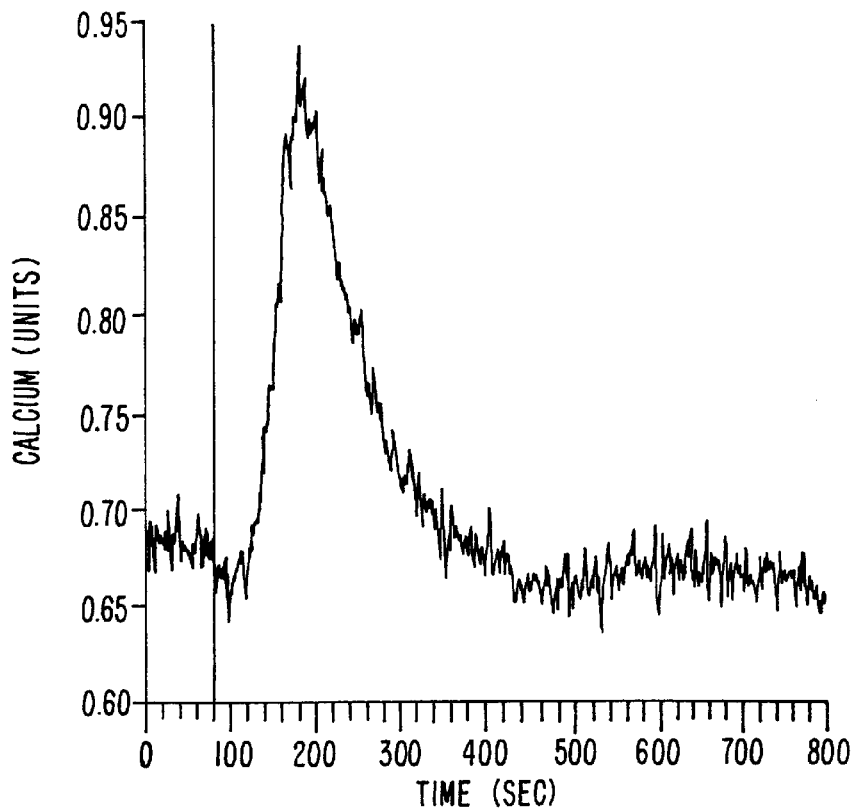
FIG. 2 shows the effect of PDGF on $[Ca^{2+}]i$ on A172 cells pretreated with ciglitazone (2 μg/ml).

The effect of PDGF on $[Ca^{2+}]i$ on A172 cells pretreated with ciglitazone (2 μg/ml) is shown in FIG. 2. Treatment with ciglitazone had no significant effect on the unstimulated (resting) $[Ca^{2+}]i$, or peak value attained after addition of PDGF (20 ng/ml). However, the calcium signal was truncated by abolition of the secondary sustained portion of the calcium signal, the portion caused by opening of plasma membrane calcium channels. The data shown in FIG. 2 is the sum of the signal obtained by scanning 10 adjacent cells. The vertical bar shows the time at which PDGF was added.

The effects of PDGF and ciglitazone on various parameters relating to $[Ca^{2+}]i$ are summarized in Table III. The data was obtained by independently evaluating each of the 8 and 10 cells shown in FIGS. 1 and 2, respectively. The data in Table III confirms the lack of a significant effect by ciglitazone on the pre-peak delay or the initial calcium peak response. On the other hand, the prolonged post-peak elevation in $[Ca^{2+}]i$ was virtually eliminated at this concentration of ciglitazone (FIG. 1). These data indicate that the effect of ciglitazone was maximal at the concentration used (2 μg/ml).

TABLE III

Effect of ciglitazone on the calcium signal induced by platelet-derived growth factor

| Parameter | Control<br>20 ng/ml PDGF<br>(n = 8) | Ciglitazone (2 μg/ml)<br>+ 20 ng/ml PDGF<br>(n = 10) |
|---|---|---|
| Baseline calcium ratio* | 0.67 +/− 0.01 | 0.68 +/− 0.01 |
| Pre-peak dalay (sec) | 57 +/− −6 | 54 +/− 5 |
| Peak response (sec) | 1.0 +/− 0.1 | 1.1 +/− 0.1 |
| Response duration (sec) | 701 +/− 37** | 172 +/− 15** |

*Calcium concentration is expressed as the ratio of Ca2+:indo 1 chelate to free (umcomplexed) indo 1. Absolute concentration of free calcium is proportional to this ratio. The PDGF used in these studies is the purifeid BB homodimer (G, Pierce, Amgen Biologicals, Thousand Oaks, CA). The vehicle for ciglitazone was used in control experiments. See text for further details.
**Significance between control and ciglitazone-treated cells was $p < 0.001$, as determined by Student's paried t-test.

The possibility that ciglitazone directly blocked PDGF-sensitive calcium channels was tested using the manganese maneuver in A172 cells loaded with indo- 1 (Szollosi et al., supra). Partial quenching of the second phase calcium response suggested partial direct blockade of the PDGF-operated calcium channel. Because, at the concentration of ciglitazone used, complete blockade of the second phase calcium response was achieved, the fact that a post-receptor effect of the drug is an inescapable conclusion. These seemingly disparate effects may simply be explained by a yet to be defmed structuraVfunctional relationship between the agonist receptor and the coordinate ROCC. Genetic uniqueness in either or both of agonist/receptor or coupled calcium channel response could, in a general sense confer the molecular organization required for the kind of diversity obviously inherent in biological signals conveyed via ROCCs.

Similar experiments on the A172 glioma cells were conducted with bradykinin, another hormone that transmits its signal via increased $[Ca^{2+}]i$. The results were similar, namely, that ciglitazone blocked the second phase sustained plateau of $[Ca^{2+}]i$ without significant effect on the initial peak response. Interestingly, bradykinin has a vaso-relaxing effect on the vasculature, quite opposite to that of PDGF which is a vasoconstrictor. Furthermore, bradykinin has analgesic effects via effects on the central nervous system. Therefore, because of our findings with bradykinin and A172 cells, we also claim that thiazoles, appropriately designed, will prove a potential repository of therapeutically efficacious analgesic medicines.

The findings described herein demonstrate that ciglitazone blocks the portion of the PDGF-stimulated calcium transient which is mediated by receptor-operated calcium channels in the plasma membrane of A172 human glioblastoma cells. The fact that the other parameters (phases) of the calcium signal remained unaffected strongly suggests that the effect of ciglitizone is highly selective.

Identical experiments were carried out on cultured A10 rat vascular smooth muscle cells (VSMC). The results were virtually identical to those obtained with the A172 cells, namely that ciglitazone eliminated the secondary sustained phase of the calcium transient induced by PDGF in VSMC. Again, the effect of the ciglitazone appeared to be maximal at the concentration used (2 μg/ml).

B. Effect on DNA synthesis.

Ciglitazone inhibited PDGF-stimulated thymidine incorporation by approximately 55% as shown in Table IV. The inhibitory effects were similar at both drug concentrations, viz 0.5 and 2.0 μg/ml. These findings suggest that ciglitazone inhibits DNA synthesis induced by PDGF. This is believed to be a consequence of the antagonist effect of the drug on PDGF operated calcium channels and suggests that ciglitazone would be expected to inhibit cell growth, proliferation, and/or migration via this effect.

These data further suggest that blockade of PDGF receptor-operated calcium channels maybe ageneral property of the thiazoles, thus making them anovel class of calcium antagonists. While the precise mechanism is unknown the early data suggests a partial direct blockage of calcium entry across the cell membrane in cells having ROCCs. These findings imply that this novel class of calcium channel blockers may have therapeutic efficacy in a variety of cardiovascular pathologies, including hypertension, cardiac arrhythmia, coronary artery spasm, and atherosclerotic vascular disease.

TABLE IV

Effect of ciglitazone on the incorporation of [$^3$H]-thymidine into human A172 glioma cells

| Serum (%) | DMSO (%) | Ciglitazone (μg/ml) | PDGF (ng/ml) | [$^3$H]-thymidine incorporation (counts per minute) |
|---|---|---|---|---|
| 10.0 | none | none | none | 2670 |
| 0.1 | none | none | none | 840 |
| 0.1 | 0.5 | none | none | 910 |
| 0.1 | none | 0.5 | none | 800 |
| 0.1 | none | 2.0 | none | 780 |
| 0.1 | none | none | 10.0 | 1560 |
| 0.1 | 0.5 | none | 10.0 | 1490 |
| 0.1 | none | 0.5 | 10.0 | 1090 |
| 0.1 | none | 2.0 | 10.0 | 1180 |

NB: The values shown represent the mean of triplicate determinations (internal error <10.0%). See text for further details.

It will be apparent to those of skill in the art that the present invention adds to the state of the art the discovery of an entire new class of ROCC antagonists useful in the treatment of a variety of disease states and the consequences of such disease.

Although the present invention has been described in some detail for the purposes of clarity and understanding, it will be obvious to those skilled in the art that certain changes and modifications may be practiced within the scope of the appended claims.

What is claimed is:

1. A method for treating vascular restenosis after angioplasty comprising administering to a patient in need thereof a dose of an antidiabetic thiazole compound in an amount effective to inhibit progression of the disease with the proviso that the thiazole bears a oxo or imino at position 4 of the thiazole ring.

2. A method of claim 1 wherein the thiazole is a thiazolidinedione.

3. A method for treating vasculoproliferative occlusive disease in a nondiabetic patient comprising administering a dose of an antidiabetic thiazole compound in an amount effective to inhibit progression of the disease to the patient wherein the anti-diabetic thiazole is a 5-aryl substituted thiazolidine derivative of formula I

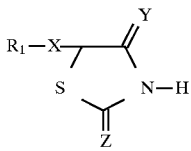

where: $R_1$ is an aromatic carbocyclic or an aromatic heterocyclic;

X is a lower alkylene or a bond; or —HC=CH—

Y is oxo or imino;

Z is oxo or imino;

and pharmaceutically acceptable salts thereof.

4. A method of claim 3 wherein the thiazolidine derivative is a thiazolidine-dione having both Y and Z are oxo.

5. A method of claim 3 wherein the thiazolidine derivative is further selected from compounds where $R_1$ is an aromatic carbocyclic and X is a lower alkylene radical.

6. A method of claim 5 wherein the thiazolidine derivative is selected from compounds wherein $R_1$ is of the formula IIa

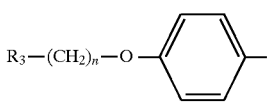

where $R_3$ is of the formula IIb

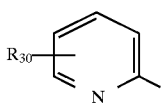

where $R_{30}$ is a lower alkyl of 1–4 carbons; or, where $R_3$ is of the formula 11c

where $R_{31}$ is a hydrogen or lower alkyl of 1–4 carbons and the cyclohexane ring may be optionally substituted with a single oxo or hydroxy, where $R_3$ is of the formula IId

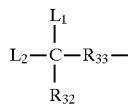

wherein $R_{32}$ is alkyl, cycloalkyl, phenylalkyl, phenyl, a five- or six-membered heterocyclic group having one or two hetero-atoms selected from the group consisting of nitrogen, oxygen and sulfur, or a group of the formula IIe

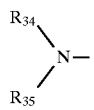

where $R_{34}$ and $R_{35}$ are the same or different and each is lower alkyl; $R_{33}$ is a bond or a lower alkylene group, $L_1$ and $L_2$ may be the same or different and each is a lower alkyl or $L_1$ and $L_2$ are combined to each other to form an alkylene group, and provided that when $R_{32}$ is other than alkyl, $L_1$ and $L_2$ may further be hydrogen, respectively.

7. A method of claim 3 wherein the compounds are selected from the group consisting of:

5-[4-(6-hydroxy-2,5,7,8-tetramethylchroman-2-yl methoxy)benzyl]thiazolidine-2,4-dione;

5-[4-(6-hydroxy-5,7,8-tetramethylchroman-2-yl methoxy)benzyl]thiazolidine-2,4-dione;

5-[4-6-hydroxy-5,7-diisopropyl-2-methylchroman-2-yl methoxy) benzyl]thiazolidine-2,4-dione and a pharmaceutically acceptable salt thereof.

8. A method of claim 3 wherein the compounds are selected from the group consisting of:

5-[(2-benzyl-2,3-dihydrobenzofuran-5-yl) methyl] thiazolidine-2,4-dione and 5-[(2-benzyl-3,4-dihydro-2H-benzopyran-6-yl)methyl] thiazolidine-2,4-dione and a pharmaceutically acceptable salt thereof.

9. A method of claim 6 where $R_{32}$ is a five or six member heterocyclic group of the formula IIf

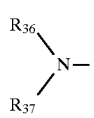

wherein $R_{36}$ and $R_{37}$ are independently lower alkyls which are combined to each other either directly or as interrupted by a hetero-atom selected from the group consisting of nitrogen, oxygen and sulfur.

10. A method of claim 3 wherein the $R_1$ is of formula VII

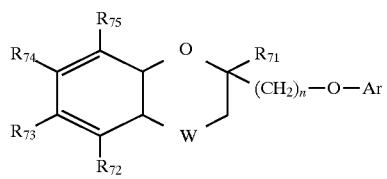

wherein:

$R_{71}$ represents: a hydrogen atom, a $(C_1-C_{25})$ alkyl group, a $(C_3-C_{10})$ cycloalkyl group or a substituted $(C_3-C_{10})$ cycloalkyl group having at least one $(C_1-C_6)$ alkyl substituent;

$R_{72}$, $R_{74}$ and $R_{75}$ are the same or different and each represents: a hydrogen atom; a $(C_1-C_{25})$ alkyl group; a substituted $(C_1-C_{26})$ having at least one of substituents (a); an aralkyl group; a $(C_3-C_{10})$ cycloalkyl group; a substituted $(C_3-C_{10})$ cycloalkyl group having at least one ($C_1$–$C_6$) alkyl substituent; an aryl group; a halogen atom; a hydroxy group; a protected hydroxy group in which the protecting group is selected from substituents (b); a ($C_1$–$C_7$) alkanoyl group; a substituted ($C_2$–$C_7$) alkanoyl group having at least one of substituents (c); an arylcarbonyl group; a cycloalkylcarbonyl group in which the cycloalkyl part is ($C_3$–$C_{10}$); a substituted cycloalkylcarbonyl group in which the cycloalkyl part is ($C_3$–$C_{10}$) and has at least one ($C_1$–$C_6$) alkyl substituent; a carboxy group; a ($C_2$–$C_7$) alkoxycarbonyl group; an aryloxycarbonyl group; and aralkyloxycarbonyl group; a nitro group; a group of formula VIIb

VIIb in which $R_{77}$ and $R_{78}$ are the same or different and each represents a hydrogen atom, a ($C_1$–$C_6$) alkyl group, an aralkyl group, a ($C_3$–$C_{10}$) cycloalkyl group, an aryl group, a ($C_1$–$C_7$) alkanoyl group, an aralkanoyl group, an arylcarbonyl group or a ($C_2$–$C_7$) alkoxycarbonyl group, or $R_{77}$ and $R_{78}$, together with the nitrogen atom to which they are attached, form a nitrogen-containing heterocyclic group having from 5 to 10 ring atoms, of which one is said nitrogen atom and from 0 to 3 are additional nitrogen and/or oxygen and/or sulphur hetero-atoms; or a group of formula VIIc

VIIc in which $R_{77*}$ and $R_{78*}$ are the same or different and each represents a hydrogen atom, a ($C_1$–$C_6$) alkyl group, an aralkyl group, a ($C_3$–$C_{10}$) cycloalkyl group or an aryl group or $R_{77}$ and $R_{78}$, together with the nitrogen atom to which they are attached, form a nitrogen-containing heterocyclic group having from 5 to 10 ring atoms, of which one is said nitrogen atom and from 0 to 3 are independently additional nitrogen or oxygen or sulphur hetero-atoms;

$R_{73}$ represents a hydrogen atom, a ($C_1$–$C_{25}$) alkyl group, a substituted ($C_1$–$C_{25}$) alkyl group having at least one of substituents (a), an aralkyl group, a ($C_3$–$C_{10}$) cycloalkyl group, a substituted ($C_3$–$C_{10}$) cycloalkyl group having at least one ($C_1$–$C_6$) alkyl substituent, an aryl group, a halogen atom, a ($C_1$–$C_7$) alkanoyl group, a substituted ($C_2$–$C_7$) alkanoyl group having at least one of substituents (c), an arylcarbonyl group, a cycloalkylcarbonyl group in which the cycloalkyl pat is ($C_3$–$C_{10}$), a substituted cycloalkylcarbonyl group in which the cycloalkyl part is ($C_3$–$C_{10}$) and has at least one ($C_1$–$C_6$) alkyl substituent, a carboxy group, a ($C_2$–$C_7$) alkoxycarbonyl group, an aryloxycarbonyl group, an aralkyloxycarbonyl group, a nitro group, a group of formula VIIb, as defined above, or.a group of formula VIIc, as defined above; or a hydroxy group, or a protected hydroxy group in which the protecting group is selected from substituents (b), provided that at least one of $R_{72}$, $R_{74}$ and $R_{75}$ represents a substituted alkyl group having at least one of substituents (a), a halogen atom, a hydroxy group, a substituted alkoxy group having at least one of substituents (c), a ($C_1$–$C_7$) alkanoyloxy group, a substituted ($C_2$–$C_7$) alkanoyloxy group having at least one of substituents (c), an arylcarbonyloxy group, a sulphoxy group, a ($C_1$–$C_7$) alkanoyl group, a substituted ($C_2$–$C_7$) alkanoyl group having at least one of substituents (c), a cycloalkylcarbonyl group in which the cycloalkyl part is, a substituted cycloalkylcarbonyl group in which the cycloalkyl part is ($C_3$–$C_{10}$) and has at least one ($C_1$–$C_8$) alkyl substituent, an arylcarbonyl group, a carboxy group, a ($C_2$–$C_7$) alkoxycarbonyl group, an aryloxycarbonyl group, an aralkyloxycarbonyl group, a nitro group, a group of formula VIIb, as defined above, or a group of formula VIIc, as defined above, Ar represents a divalent aromatic carbocyclic group or a divalent aromatic heterocyclic group;

W represents a methylene group, a carbonyl group, a group of formula >CH—OY in which Y represents a hydrogen atom, a ($C_1$–$C_7$) alkanoyl group or an arylcarbonyl group, or a group of formula >C=N—OV in which V represents a hydrogen atom, a ($C_1$–$C_6$) alkyl group, a substituted ($C_1$–$C_6$) alkyl group having at least one of substituents (c), a ($C_1$–$C_7$) alkanoyl group or an arylcarbonyl group; and n represents an integer from 1 to 10; and wherein said aralkyl groups have an alkyl portion containing from 1 to 6 carbon atoms and an aryl portion as defined below, the alkyl portion being unsubstituted or having at least one of substituents (c);

wherein substituents (a) are:

hydroxy groups; protected hydroxy groups in which the protecting group is selected from substituents (b); ($C_1$–$C_7$) aliphatic carboxylic acyl groups; ($C_2$–$C_7$) aliphatic carboxylic acyl groups having at least one of substituents (c); arylcarbonyl groups; cycloalkylcarbonyl groups in which the cycloalkyl part is ($C_3$–$C_{10}$); substituted cycloalkylcarbonyl groups in which the cycloalkyl part is ($C_3$–$C_{10}$) and having at least one ($C_1$–$C_6$) alkyl substituent; carboxy groups; ($C_2$–$C_7$) alkoxycarbonyl groups; aryloxycarbonyl groups; aralkyloxycarbonyl groups; hydroxyimino groups; protected hydroxyimino groups in which the protecting group is selected from substituents (b); groups of formula VIIb, as defined above; and groups of formula VIIc, as defined above;

wherein substituents (b) are:

($C_1$–$C_6$) alkyl groups, substituted ($C_1$–$C_6$) alkyl groups having at least one of substituents (c), ($C_1$–$C_7$) aliphatic carboxylic acyl groups, substituted ($C_2$–$C_7$) aliphatic carboxylic acyl groups having at least one of substituents (c), arylcarbonyl groups, ($C_2$–$C_7$) alkoxycarbonyl groups, aryloxycarbonyl groups, groups of formula (VIIc), as defined above and sulpho groups;

wherein substituents (c) are:

carboxy groups, ($C_2$–$C_7$) alkoxycarbonyl groups and aryl groups;

said aryl groups and the aryl parts of said aralkyl, arylcarbonyl, aryloxycarbonyl, aralkyloxycarbonyl and divalent aromatic groups being ($C_6$–$C_{14}$) carbocyclic aryl groups which are unsubstituted or have at least one of substituents (d);

said heterocyclic groups, heterocyclic parts of said heterocyclic acyl and acyloxy groups and said divalent heterocyclic aromatic groups have from 5 to 14 ring atoms, of which from 1 to 5 are independently nitrogen, oxygen or sulphur hetero-atoms, said heterocyclic groups being unsubstituted or having at least one substituent selected from substituents (d) and substituents (e);

wherein substituents (d) are:

($C_1$–$C_6$) alkyl groups, ($C_1$–$C_6$) alkoxy groups, hydroxy groups, sulphoxy groups, halogen atoms, nitro groups, groups of formula (II), as defined above, $(C_1-C_7)$ aliphatic carboxylic acyl groups, $(C_7-C_{11})$ arylcarbonyloxy groups in which the aryl part is unsubstituted or has at least one substituent selected from $(C_1-C_6)$ alkyl groups, $(C_1-C_6)$ alkoxy groups and halogen atoms;

wherein substituents (e) are:

aryl groups and oxygen atoms.

11. A method of claim 3 wherein the $R_1$ is of formula VII

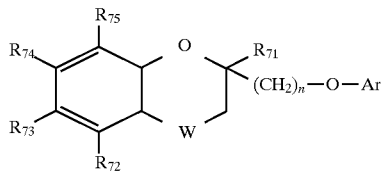

VII wherein:

$R_{71}$ represents: a hydrogen atom, a $(C_1-C_{25})$ alkyl group;

$R_{72}$, $R_{74}$ and $R_{75}$ are the same or different and each represents: a hydrogen atom; a $(C_1-C_{25})$ alkyl group;

$R_{73}$ represents a hydrogen atom, a $(C_1-C_{25})$ alkyl group, or a hydroxy group;

Ar represents a divalent aromatic carbocyclic group or a divalent aromatic heterocyclic group;

W represents a methylene group, a carbonyl group, a group of formula >CH—OY in which Y represents a hydrogen atom, a $(C_1-C_7)$ alkanoyl group or an arylcarbonyl group and n represents an integer from 1 to 10.

* * * * *